United States Patent
Charles

(10) Patent No.: US 10,702,415 B2
(45) Date of Patent: Jul. 7, 2020

(54) SURGICAL APPARATUS INCLUDING ASPIRATION DEVICE SENSORS

(71) Applicant: NOVARTIS AG, Basel (CH)

(72) Inventor: Steven T. Charles, Germantown, TN (US)

(73) Assignee: Alcon Inc., Fribourg (CH)

( * ) Notice: Subject to any disclaimer, the term of this patent is extended or adjusted under 35 U.S.C. 154(b) by 292 days.

(21) Appl. No.: 15/239,979

(22) Filed: Aug. 18, 2016

(65) Prior Publication Data

US 2018/0049920 A1 Feb. 22, 2018

(51) Int. Cl.
*A61F 9/007* (2006.01)
*A61M 1/00* (2006.01)

(52) U.S. Cl.
CPC ....... *A61F 9/00745* (2013.01); *A61M 1/0025* (2014.02); *A61M 1/0031* (2013.01); *A61M 1/0058* (2013.01); *A61M 1/0064* (2013.01); *A61B 2217/005* (2013.01); *A61B 2217/007* (2013.01); *A61M 1/0086* (2014.02); *A61M 2205/3306* (2013.01); *A61M 2205/3317* (2013.01); *A61M 2205/3331* (2013.01); *A61M 2205/3334* (2013.01); *A61M 2205/3341* (2013.01); *A61M 2210/0612* (2013.01)

(58) Field of Classification Search
CPC ............. A61F 9/00745; A61M 1/0064; A61M 1/0031; A61M 1/0058; A61M 1/0086; A61M 2210/0612; A61M 2205/3306; A61M 2205/3331; A61M 2205/3341; A61B 2217/007; A61B 2217/005

See application file for complete search history.

(56) References Cited

U.S. PATENT DOCUMENTS

| | | | |
|---|---|---|---|
| 4,650,461 A | * | 3/1987 | Woods ............... A61F 9/00736 604/28 |
| 7,524,299 B2 | | 4/2009 | Hopkins |
| 8,465,467 B2 | | 6/2013 | Gao |
| 8,617,106 B2 | | 12/2013 | Zacharias |
| 9,314,553 B2 | | 4/2016 | Gordon |
| 9,549,850 B2 | | 1/2017 | Sorensen |
| 9,549,851 B2 | | 1/2017 | Chon |
| 9,561,321 B2 | | 2/2017 | Sorensen |
| 10,052,228 B2 | | 8/2018 | Boukhny |
| 10,314,741 B2 | | 6/2019 | Sorensen |
| 10,314,953 B2 | | 6/2019 | Ovchinnikov |
| 2002/0016569 A1 | * | 2/2002 | Critchlow ......... A61M 5/14546 604/131 |
| 2002/0115936 A1 | * | 8/2002 | Koblanski ............ A61B 5/0205 600/481 |
| 2008/0319451 A1 | * | 12/2008 | Zacharias ........... A61F 9/00736 606/107 |
| 2011/0034864 A1 | * | 2/2011 | Dacquay ............. A61M 3/0212 604/28 |
| 2014/0163455 A1 | | 6/2014 | Wilson et al. |
| 2015/0202081 A1 | | 7/2015 | Eichler |
| 2016/0089268 A1 | | 3/2016 | Chon et al. |

(Continued)

*Primary Examiner* — Erich G Herbermann

(57) ABSTRACT

A method and system provide a surgical hand piece including an aspiration line, a tip and a sensor. The tip is coupled with the aspiration line. The sensor is in the aspiration line. The sensor measures a change in at least one of flow through the aspiration line, pressure in the aspiration line and motion of an additional portion of the hand piece within the aspiration line.

15 Claims, 3 Drawing Sheets

(56) References Cited

U.S. PATENT DOCUMENTS

2066/0089268     3/2016  Chon et al.
2017/0326000 A1  11/2017 Heeren
2018/0207032 A1   7/2018 Charles
2018/0296391 A1  10/2018 Charles
2019/0282401 A1   9/2019 Sorensen

* cited by examiner

SURGICAL APPARATUS INCLUDING ASPIRATION DEVICE SENSORS

FIELD

The present disclosure relates generally ophthalmic surgery and, more particularly, to a surgical apparatus including aspiration device sensors.

BACKGROUND

Ophthalmic surgery frequently involves the removal of fluid and/or tissue from the eye via a surgical hand piece or connector to a cannula. The surgical hand piece includes a tip, an aspiration line, an irrigation line and associated electronics. The aspiration and irrigation lines are connected with the tip. The tip has the appropriate devices for the procedure being performed. Fluid and/or tissue is removed via the aspiration line, while the irrigation line provides fluid to the eye. The surgical hand piece or cannula is also connected to and controlled by a console. The aspiration line is connected to the tip and to tubing coupled to a vacuum pump controlled by the console. Similarly, the infusion line is connected to the tip and to tubing coupled to a fluid source. The vacuum pump and fluid source are typically remote from the surgical hand piece and may be part of the console. For example, the vacuum pump and other portions of the console may be several feet from the surgical hand piece. In operation, the tip is inserted into the patient's eye. A vacuum is applied to the aspiration line in order to remove material from the eye. Fluid is also provided to the eye via the infusion line, allowing the intraocular pressure of the eye to be maintained.

Although the ophthalmic surgery may be performed, there is a danger of the eye collapsing during surgery. For example, in cataract surgery, the cataract is broken up and removed from the patient's eye. The console controls piezoelectric transducers in the surgical hand piece that cause a cutting tip to oscillate at ultrasonic frequencies, breaking up the cataract. A large diameter port in the tip is coupled to the aspiration line. The vacuum pump, typically peristaltic, applies a large negative pressure to tubing connected to the aspiration line in order to remove the dense cataract tissue. The pieces of the cataract, vitreous humor and other tissue flow out of the eye through the port and aspiration line. Fluid also flows into the eye through the irrigation line. However, tissue may occlude the port. At some point, the tissue blocking the port breaks up and passes through the aspiration line. As a result, there is a sudden, large increase in the outflow of material from the eye and a corresponding high vacuum in the aspiration line. The inflow of fluid generally cannot keep up with this flow. The eye may then collapse around the tip, which is highly undesirable.

A similar issue exists in the extraction of silicone oil from the eye. In some surgeries, a viscous fluid, such as silicone oil, may be injected into the eye to support the eye during healing. Later, the silicone oil is extracted. In this case, the hand piece acts as a syringe. The tip includes a cannula that is inserted into the patient's eye. A piston resides in the aspiration line. A vacuum pump controlled via the console applies a negative pressure to the aspiration line and, therefore, the portion of the piston distal from the cannula. In response, the piston moves along the aspiration line and the silicone oil may be extracted through the cannula and into the aspiration line. Simultaneously, the infusion line provides fluid to the eye to maintain the intraocular pressure of the eye. The viscosity of the silicone oil is typically several orders of magnitude greater than that of the vitreous humor. Consequently, when the last of the silicone oil is removed, there is a rapid change in the viscosity of the fluid entering the tip. If the vacuum applied to the piston is not changed, the piston will suddenly increase its speed. A relatively large volume of fluid may then be rapidly extracted from the eye. The inflow from the irrigation line generally cannot keep up with this rapid outflow. Again, the eye may collapse.

In order to prevent collapse of the eye in the above situations, the surgeon must rapidly decrease the vacuum applied to the aspiration line in response to seeing the pressure drop in the aspiration line or the last of the silicone oil removed. Consequently, the surgeon constantly monitors the status of the eye and must quickly respond to a change in the flow of fluid from the eye. This may be difficult. Even if the surgeon is vigilant, decreasing the vacuum in the aspiration line is still subject to human response time, which may be relatively long (over 400 hundred milliseconds). As a result, the eye may still collapse.

Accordingly, what is needed is a mechanism for assisting a physician in ophthalmic surgery in which fluid, tissue and/or other material is removed from the eye.

BRIEF SUMMARY OF THE INVENTION

A method and system provide a surgical hand piece including an aspiration line, a tip and a sensor. The tip is coupled with the aspiration line. The sensor is in the aspiration line. The sensor measures a change in at least one of flow through the aspiration line, pressure in the aspiration line and motion of an additional portion of the hand piece within the aspiration line.

According to the method and system disclosed herein, changes in the pressure, flow and/or motion of items such as a piston in the aspiration line may be detected by the sensor. Signal(s) from the sensor can be used reduce the vacuum applied to the aspiration line. Consequently, the pressure in the eye may better maintained within tolerances, patient safety improved and the burden on the surgeon reduced.

BRIEF DESCRIPTION OF SEVERAL VIEWS OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION OF THE PREFERRED EMBODIMENTS

Figure 1A:
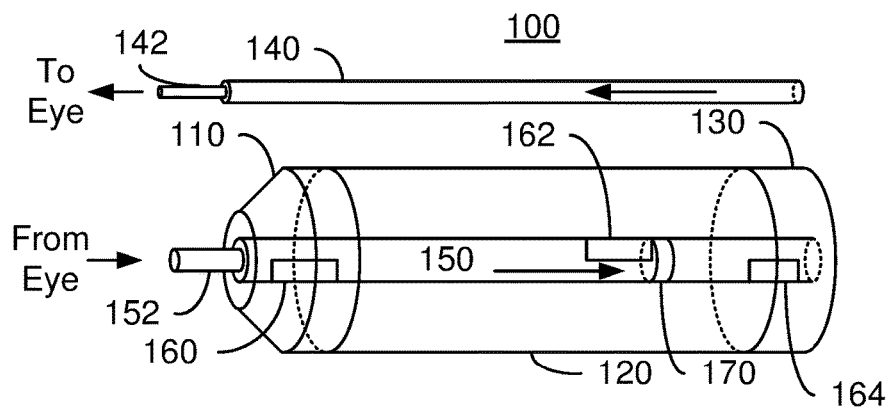
FIGS. 1A and 1B are diagrams depicting an exemplary embodiment of a surgical hand piece including sensors in the aspiration line and the surgical hand piece used in conjunction with a console.

The exemplary embodiments relate to surgical hand pieces, such as those used in ophthalmic surgery. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

The method and system are also described in terms of singular items rather than plural items. For example, a single sensor is used and/or shown in some embodiments. One of ordinary skill in the art will recognize that these singular terms encompass plural. For example, multiple sensors might be used.

In certain embodiments, the system includes one or more processors and a memory. The one or more processors may be configured to execute instructions stored in the memory to cause and control the process set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Furthermore, aspects of the method and system may take the form of a software component(s) executed on at least one processor and which may be embodied in one or more computer readable medium(s) having computer readable program code embodied thereon.

A method and system provide a surgical hand piece including an aspiration line, a tip and a sensor. The tip is coupled with the aspiration line. A portion of the tip is configured to be inserted into a patient's eye or a cannula connector. The sensor is in the aspiration line. The sensor measures a change in at least one of flow through the aspiration line, pressure in the aspiration line and motion of an additional portion of the hand piece within the aspiration line.

Figure 1B:
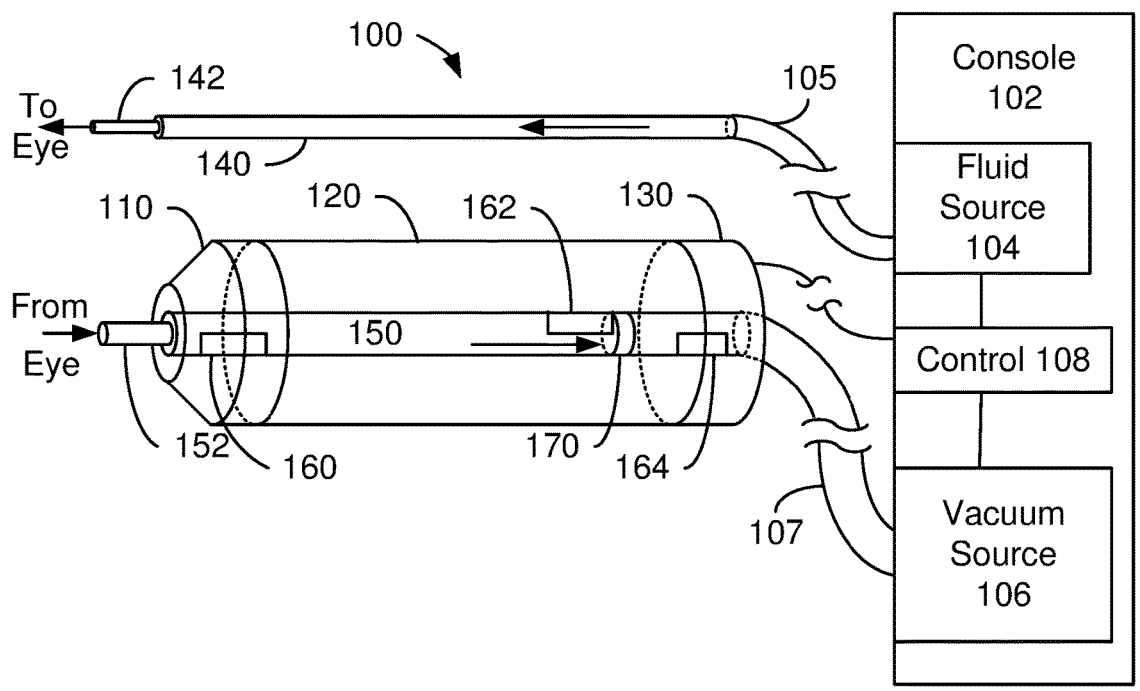

FIGS. 1A and 1B depict a side view of an exemplary embodiment of a surgical hand piece 100 usable in ophthalmic surgery and the surgical hand piece 100 when used in conjunction with a console 102. FIGS. 1A and 1B are not to scale and for explanatory purposes only. Thus, a particular hand piece is not intended to be shown. As described herein, a surgical hand piece includes any component usable in ophthalmic surgery in which an aspiration line is present. For example, the term surgical hand piece includes but is not limited to an aspiration line that may be connected to a cannula. Such an aspiration line may be inserted through a sclerotomy cannula or a silicone rubber sleeve over the sclerotomy cannula. Thus, the surgical hand piece could be considered to include the aspiration line; the aspiration line and cannula; or the aspiration line, cannula, sclerotomy cannula and silicone rubber sleeve, if present. Alternatively, the surgical hand piece might include a more traditional surgical hand piece including a rigid housing through which the aspiration line 150 runs. The surgical hand piece 100 may be an ultrasonic hand piece, or fragmenter, used in surgeries such as cataract removal. In other embodiments, the surgical hand piece 100 may be a viscous fluid controller (VFC) that functions as a syringe. However, the surgical hand piece 100 may be another type of surgical hand piece capable of removing fluid, tissue and/or other material from the operating field.

The surgical hand piece 100 includes a tip 110, a body 120 and may include a cap 130. The hand piece 100 also includes an aspiration line 150. Also shown is a separate irrigation line 140. In some embodiments, the irrigation line 140 may be integrated with the remainder of the hand piece 100. Although described as an irrigation line 140, the irrigation line 140 may also be known as an infusion line, for example if used in vitreoretinal surgery. The aspiration line 150 is considered to extend through the cap 130, body 120 and tip 110. In practice, however, the aspiration line 150 may include separate components in each of the sections 110, 120 and 130. For example, the portion of the aspiration line 150 residing in the tip 150 may be separable from the portion(s) of the aspiration line 150 in the body 120 and/or cap 130. The aspiration line 150 and irrigation line 140 each includes a line 152 and 142, respectively, that may be inserted into the eye (not shown). Alternatively, the line 152 and/or 142 may be inserted into a cannula connector for a cannula that is inserted into the eye. The lines 142 and 152 may be considered ports or cannula. In some embodiments, the body 120 may consist of the aspiration line 150. In such embodiments, the cap 130 may simply be used to connect other components, such as tubing, to the aspiration line. In such embodiments, the tip 110 may simply be used to connect a cannula 152 to the aspiration line 150. Also shown is optional additional component 170 that may reside in the aspiration line 150. The additional component 170 may be a piston if the hand piece 100 is a VFC. In another embodiment, the additional component 170 may have another shape, another function and/or another location. In other embodiments, the additional component 170 may be omitted.

Also shown in FIGS. 1A and 1B are sensors 160, 162 and 164. Although three sensors 160, 162 and 164 are shown, in other embodiments, another number of sensors may be used. Sensor 160 is shown in the tip 110. Sensor 162 is shown in the body 120. Sensor 164 is shown in the cap 130. However, nothing prevents one or more of the sensors 160, 162 and/or 164 from being omitted or placed in a different location. For example, two sensors 160 and 162 may reside in the tip 110.

The sensors 160, 162 and 164 are used to monitor flow from the eye. More specifically, the sensors 160, 162 and 164 measure flow through the aspiration line 150, pressure in the aspiration line 150 and/or motion of an additional portion of the hand piece within the aspiration line 150. As used herein, measurement of a pressure includes measurement of a vacuum (amount below ambient/room pressure). For example, the sensor 160 may be a pressure sensor, the sensor 162 might be a motion sensor and the sensor 164 might be a flow sensor. Alternatively, all sensors 160, 162 and 164 might be pressure sensors. In another embodiment, all of the sensors 160, 162 and 164 might be motion sensors. Other configurations of the sensors 160, 162 and 164 might be present. The quantity measured by the sensors 160, 162 and 164 may depend upon the function of the hand piece 100. For example, if the hand piece 100 is a fragmenter used in breaking up and removing cataracts, then one or more of the sensors 160, 162 and 164 may be pressure sensors. If the hand piece 100 is used as a syringe, for example in removal of silicone oil, then the sensor 162 might be attached to the component 170 and may provide a measurement of the motion of the component 170. For example, the sensor 162 may measure the speed of the component 170. Such a sensor 162 may be a Hall effect sensor or encoder, an accelerometer, and/or an optical motion sensor. When pressure and motion are measured, the sensors 160, 162 and 164 may still be viewed as measuring flow through the aspiration line 150 because the pressure in the aspiration line 150 and speed of the component 170 may affect flow of material through the aspiration line 150. Note that although no sensor is shown in the irrigation line 140, in other embodiments, one or more analogous sensors might be included in the irrigation line 140.

The sensors 160, 162 and 164 might provide a quasi-quantitative measure of flow, pressure or motion in the aspiration line 150. Stated differently, the sensors 160, 162 and/or 164 are capable of measuring large changes in the flow, pressure or motion in the aspiration line 150. In some embodiments, the sensors 160, 162 and/or 164 may measure a change of at least fifty percent in the flow, pressure and/or speed of material in the aspiration line 150. In some such embodiments, a change of at least one hundred percent in the flow, pressure and/or speed of material in the aspiration line 150 is measurable by the sensor(s) 160, 162 and/or 164. In some embodiments, the change measurable by the sensor(s) 160, 162 and/or 164 is at least ten multiplied by the flow, pressure and/or speed of material in the aspiration line 150. However, nothing prevents the use of sensors 160, 162 and/or 164 that can measure smaller changes in pressure, flow, and/or speed.

The hand piece 100 is shown in use in FIG. 1B. The hand piece 100 is coupled with the console 102. The console 102 includes a fluid source 104, control block 108 and vacuum source 106. In other embodiments, the fluid source 104 and/or vacuum source 106 may be physically separated from the console. The control block 108 may include a processor executing instructions stored in a memory and capable of communicating with the sensors 160, 162 and/or 164. The fluid source 104 is coupled with the irrigation line 140 via tubing 105. The vacuum source 106 is coupled with the aspiration line 150 via tubing 107. The tubing 107 is connect to the aspiration line 150 by the cap 130. The vacuum source 106 may be a vacuum pump such as a peristaltic pump or analogous device. The tubing 105 and 107 are typically quite long as the console 102 is generally located relatively far from the hand piece 100 during use. For example, the tubing 105 and 107 may be on the order of eighty through 100 inches long. Other lengths are possible. A user, such as a surgeon, may control the vacuum, fluid, and/or other electronics for the hand piece 100 using the console 102.

In operation, the lines 142 and 152 may be inserted into an incision in the eye (not shown) to perform ophthalmic surgery. The surgeon may control the vacuum applied by the vacuum source 106 via a foot pedal (not shown). The vacuum source 106 provides suction that removes material from the eye. The vacuum source 106 may remove the material directly or may cause a piston, such as the optional component 170, to move. In either case, a vacuum is applied to the eye. In some embodiments, the material removed may be tissue, such as cataract or scar tissue, that is broken up by the hand piece 100. In such embodiments, the hand piece 100 functions as a fragmenter. Alternatively, the hand piece 100 may be a VFC and the material removed may be a viscous fluid such as silicone oil. In another embodiment, other foreign material(s) and/or tissues/fluid may be removed from the patient's eye. The fluid source 104 provides fluid to the irrigation line 140, which replaces the material removed from the eye with the contents of the fluid source 104.

While the vacuum is applied, the sensors 160, 162 and/or 164 sense pressure, flow and/or movement in the aspiration line 150. In some embodiments, the sensor(s) 160, 162 and/or 164 continuously provide a signal indicating the level of one or more of these quantities to the control block 108. In other embodiments, the sensor(s) 160, 162 and/or 164 continuously provide a signal indicating the level of a change in one or more of these quantities to the control block 108. Alternatively, the sensor(s) 160, 162 and/or 164 provide a signal to the control block 108 in response to some threshold being reached or exceeded for a change in the piston speed, flow, or pressure in the aspiration line. In some embodiments, the threshold is fifty percent of a particular value in the quantity. In other embodiments, the threshold is one hundred percent of the value. In still other embodiments, the threshold may be two, three or ten times the value. Thus, the threshold might be a change of fifty percent, a change of one hundred percent or a change of a higher percentage in the pressure, flow, and/or piston speed.

Based on the signal(s) provided by the sensor(s) 160, 162 and/or 164, the control block 108 controls the vacuum source. If the signal indicates that the change met or exceeded a threshold, then the control block 108 reduces the vacuum provided by the vacuum source 106 in response to receiving the signal. In other embodiments, the control block 108 may determine whether the threshold is met or exceeded and controls the vacuum source 106 based on whether the threshold is reached or exceeded. If pressure is measured, then a decrease in pressure (increase in vacuum) that meets or exceeds the threshold results in the suction provided by the vacuum source being reduced. If motion is measured, then an increase in speed of the piston 170 that meets or exceeds the threshold may result in the suction provided by the vacuum source 106 being reduced. If flow is measured, then an increase in flow that meets or exceeds the threshold may result in the suction provided by the vacuum source 106 being reduced. As a result, a change in the flow though, pressure in or movement of a component 170 within the aspiration line 150 automatically results in a change in the vacuum provided by the vacuum source 106.

The surgical hand piece 100 may have improved operation. Changes in the flow through, pressure in or speed of a component 170 within the aspiration line 150 automatically result in a change in the vacuum source 106. For example, in vitreoretinal surgery, the hand piece 100 may be used as a fragmenter. In vitreoretinal surgery, the hand piece 100 may remove dislocated cataracts after the vitreous has been removed with a vitreous cutter. In such an embodiment, the line 152 is inserted through an incision in the patient's eye. Suction is applied to the aspiration line 150 using the vacuum source 106. Tissue flows out of the eye through the aspiration line 150. Fluid may also flow into the patient's eye through the line 142 inserted in another incision. During removal, a piece of the cataract, scar tissue or other material may occlude the port 152. If such a piece of tissue occluding the port 152 is broken up and suddenly passes through the aspiration line 150, then the sensor(s) 160, 162 and/or 164 may sense a decrease in the pressure within the aspiration line 150. If this change in pressure exceeds a threshold or the pressure within the line 150 drops below a threshold, then the control block 108 automatically reduces the suction provided by the vacuum source 106.

Similarly, the hand piece 100 may be used as a VFC. In such embodiments, the hand piece 100 includes the piston 170. The vacuum source 106 applies a vacuum to the aspiration line 150, causing the piston 170 to move. The silicone oil is extracted from the eye. If the last bit of silicone oil is removed via the port 152, then subsequent material entering the port 152 may have a much lower viscosity. As a result, the piston 170 may rapidly move. The sensor 162 may sense that the speed or change in speed of the piston 170 meets or exceeds the threshold. If so, the control block 108 automatically controls the vacuum source 106 to reduce the suction provided.

Control of the vacuum source 106 by the control block 108 in these and analogous cases may be accomplished in a much shorter time frame than if a surgeon controlled the vacuum source directly. For example, the response time may be reduced from hundreds of milliseconds to less than one hundred milliseconds. Thus, such situations may be less likely to result in collapse of the patient's eye. Further, the surgeon is relieved of the burden of constantly and closely monitoring the pressure within the eye or aspiration line 150. Ophthalmic surgery may be facilitated and patient safety may be improved. Consequently, performance of the surgical hand piece 100 may be improved and the ability of a surgeon to perform procedures may be enhanced.

Figure 2:
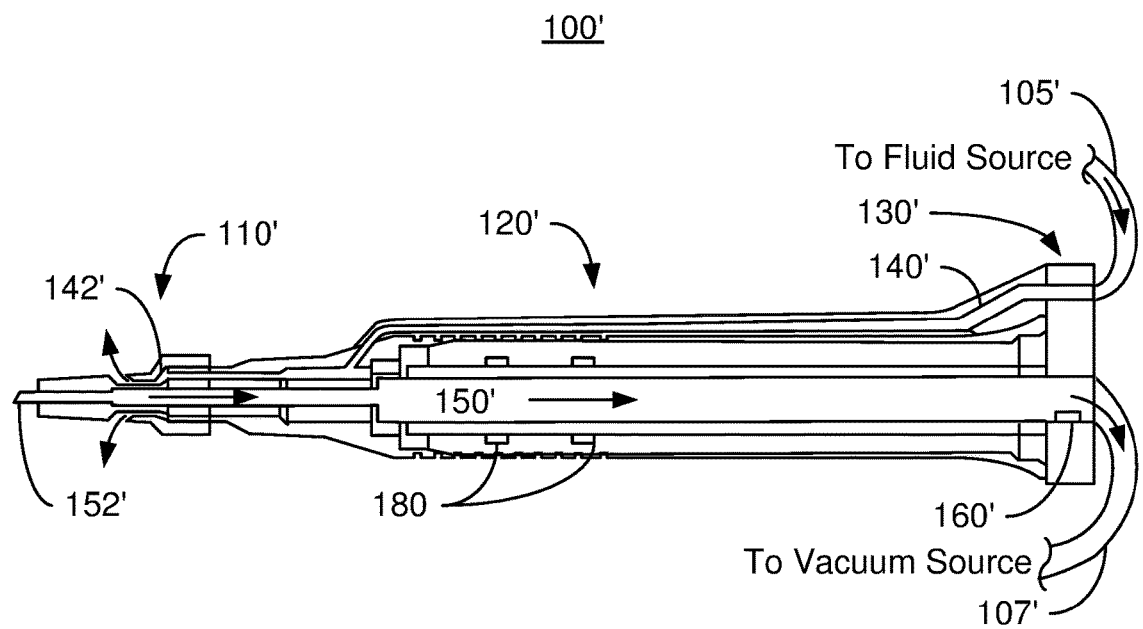
FIG. 2 depicts another exemplary embodiment of a surgical hand piece including sensors in the aspiration line.

FIG. 2 depicts a side view of another exemplary embodiment of a surgical hand piece 100' usable in ophthalmic surgery. FIG. 2 is not to scale and for explanatory purposes only. Thus, a particular hand piece is not intended to be shown. The surgical hand piece 100' may be an ultrasonic hand piece, or fragmenter, used in surgeries such as cataract removal or vitreoretinal surgery. However, the surgical hand piece 100' may be another type of surgical hand piece capable of removing fluid, tissue and/or other material from the operating field.

The surgical hand piece 100' is analogous to the surgical hand piece 100. Analogous components have similar labels. The surgical hand piece 100' includes a tip 110', a body 120' and a cap 130'. The hand piece 100' also includes an aspiration line 150' and an integrated irrigation line 140'. Thus, the hand piece 100' includes a housing as part of the body 120'. In other embodiments, such a rigid housing might be omitted. The aspiration line 150' and irrigation line 140' are considered to extend through the cap 130', body 120' and tip 110'. In practice, however, the lines 140' and/or 150' may include separate components in each of the sections 110', 120' and 130'. The aspiration line 150' and irrigation line 140' each includes a line/port 152' and 142', respectively, that may be inserted into the eye (not shown). Also shown are piezoelectric blocks 180 used to oscillate a portion of the tip, such as the line 152'. Although shown in the body 120', the piezoelectric blocks 180 may be located elsewhere. Thus, the hand piece 100' may function as a fragmenter used in ophthalmic surgery such as cataract removal. In other embodiments, the hand piece 100' may have another function.

The hand piece 100' also includes a sensor 160'. Although a single sensor 160' in a particular location in shown, in other embodiments, other sensor(s) in other location(s) may be present. The sensor 160' is shown in the cap 130', which connects the lines 140' and 150' to tubing 105' and 107', respectively. The sensor 160' is used to monitor pressure in the aspiration line 150'. Although no sensor is shown in the irrigation line 140', in other embodiments, one or more analogous sensors might be included in the irrigation line 140'.

The sensor 160' provides a quasi-quantitative measure of pressure or a change in pressure in the aspiration line 150. In some embodiments, the sensor 160' corresponds the thresholds described above. Thus, significant changes in pressure may be sensed by the sensor 160'. More specifically, a drop in pressure/increase in vacuum that meets or exceeds the thresholds may be determined by the sensor 160'.

In operation, a portion of the tip 110' including the lines 142' and 152' may be inserted into an incision in the eye (not shown) during cataract removal or other ophthalmic surgery. Thus, the line 152' may be a cannula having the appropriate gauge for removal of dislocated cataracts and/or other tissue. The surgeon may turn on the vacuum applied by the vacuum source (not shown in FIG. 2) to remove material such as a dislocated cataract from the eye. A fluid source (not shown) provides fluid which replaces the material removed from the eye to the irrigation line 140'.

While the vacuum is applied, the sensor 160' measures pressure in the aspiration line 150'. In some embodiments, the sensor 160' continuously provides a signal indicating the pressure to the control block (not shown in FIG. 2) of the console. In other embodiments, the sensor 160' continuously provides a signal indicating the level of a change in pressure to the control block. Alternatively, the sensor 160' provides a signal to the control block in response to some threshold being reached or exceeded for a change in the pressure in the aspiration line 150'. The thresholds may be the same as described above.

Based on the signal(s) provided by the sensor 160', the vacuum source is controlled. If the signal indicates that the change in pressure met or exceeded a threshold, then the vacuum provided by the vacuum source is reduced. Consequently, the pressure in the aspiration line 150' increased.

The surgical hand piece 100' may have improved operation analogous to that described above. Changes in the pressure in the aspiration line 150' quickly and automatically results in a reduction in suction applied by the vacuum source. Thus, the patient's eye may be less likely to suffer collapse. Further, the burden on the surgeon of constantly and closely monitoring the pressure within the eye or aspiration line 150' may be ameliorated. Thus, ophthalmic surgery may be facilitated and patient safety may be improved. Consequently, performance of the surgical hand piece 100' may be improved and the ability of a surgeon to perform procedures may be enhanced.

Figure 3:
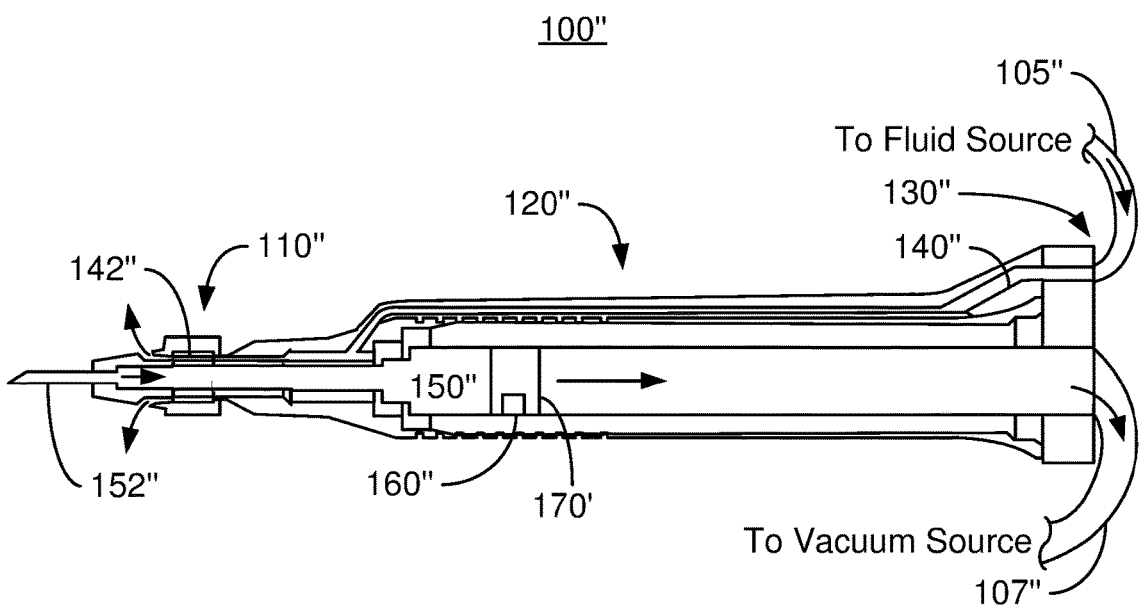
FIG. 3 depicts another exemplary embodiment of a surgical hand piece including sensors in the aspiration line.

FIG. 3 depicts a side view of another exemplary embodiment of a surgical hand piece 100" usable in ophthalmic surgery. FIG. 3 is not to scale and for explanatory purposes only. Thus, a particular hand piece is not intended to be shown. The surgical hand piece 100" may be a VFC used in removal of viscous fluid such as silicone oil. However, the surgical hand piece 100″ may be another type of surgical hand piece capable of removing fluid, tissue and/or other material from the operating field.

The surgical hand piece 100″ is analogous to the surgical hand pieces 100 and/or 100'. Analogous components have similar labels. The surgical hand piece 100″ includes a tip 110″, a body 120″ and a cap 130″. The hand piece 100″ also includes an aspiration line 150″ and an integrated irrigation line 140″. Thus, the hand piece 100″ includes a housing as part of the body 120″. In other embodiments, such a rigid housing might be omitted. The aspiration line 150″ and irrigation line 140″ are considered to extend through the cap 130″, body 120″ and tip 110″. In practice, however, the lines 140″ and/or 150″ may include separate components in each of the sections 110″, 120″ and 130″. The aspiration line 150″ and irrigation line 140″ each includes a line/port 152' and 142', respectively, that may be inserted into the eye (not shown). Also shown is free piston 170'. Thus, a vacuum is applied by the vacuum source (not shown), which moves the piston 170'. The viscous fluid may then be drawn into the aspiration line 150″ via the tip 152″.

The hand piece 100″ also includes a sensor 160″, which may be attached to the piston 170'. The sensor 160″ might be a Hall effect sensor, an accelerometer or an optical motion sensor. Although a single sensor 160″ in a particular location in shown, in other embodiments, other sensor(s) in other location(s) may be present. The sensor 160″ measures the movement of the piston 170'. More specifically, the sensor 160″ may measure the speed/velocity or change in speed/velocity of the piston 170'. Although no sensor is shown in the irrigation line 140', in other embodiments, one or more analogous sensors might be included in the irrigation line 140'.

The sensor 160″ provides a quasi-quantitative measure of speed or a change in speed of the piston 170'. In some embodiments, the sensor 160″ corresponds the thresholds described above. Thus, significant changes in speed may be sensed by the sensor 160'. More specifically, an increase in speed that meets or exceeds the thresholds may be determined by the sensor 160″.

In operation, a portion of the tip 110″ including the ports 142″ and 152″ may be inserted into an incision in the eye (not shown). Thus, the line 152″ may be a cannula having the appropriate gauge for silicone oil extraction. A vacuum is applied by the vacuum source (not shown in FIG. 2). The vacuum causes the piston 170' to move within the aspiration line 170'. Movement of the piston 170' causes a suction to be applied to the port 152″ and viscous fluid to be extracted from the eye. A fluid source (not shown) provides fluid to the irrigation line 140″, which replaces the material removed from the eye with the contents of the fluid source.

While the vacuum is applied, the sensor 160″ measures movement of the piston 170' in the aspiration line 150″. In some embodiments, the sensor 160″ continuously provides a signal indicating the piston speed to the control block (not shown in FIG. 3) of the console. In other embodiments, the sensor 160″ continuously provides a signal indicating the level of a change in speed to the control block. Alternatively, the sensor 160″ provides a signal to the control block in response to some threshold in piston speed being reached or exceeded. The thresholds may be the same as described above.

Based on the signal(s) provided by the sensor 160″, the vacuum source is controlled. If the signal indicates that the change/increase in speed met or exceeded a threshold, then the vacuum provided by the vacuum source is reduced. This may occur when the last of the viscous silicone oil is extracted from the eye. Consequently, the pressure in the aspiration line 150″ increased. The piston 170' then slows. Thus, vitreous fluid or other material desired to remain in the eye is not rapidly removed.

The surgical hand piece 100″ may have improved operation analogous to that described above. Changes in the speed of the piston 170' within the aspiration line 150″ rapidly and automatically results in a reduction in suction applied by the vacuum source. Thus, the patient's eye may be less likely to suffer collapse. Further, the surgeon is relieved of the burden of constantly and closely monitoring the pressure within the eye or aspiration line 150″. Thus, ophthalmic surgery may be facilitated and patient safety may be improved. Consequently, performance of the surgical hand piece 100″ may be improved and the ability of a surgeon to perform procedures may be enhanced.

Figure 4:
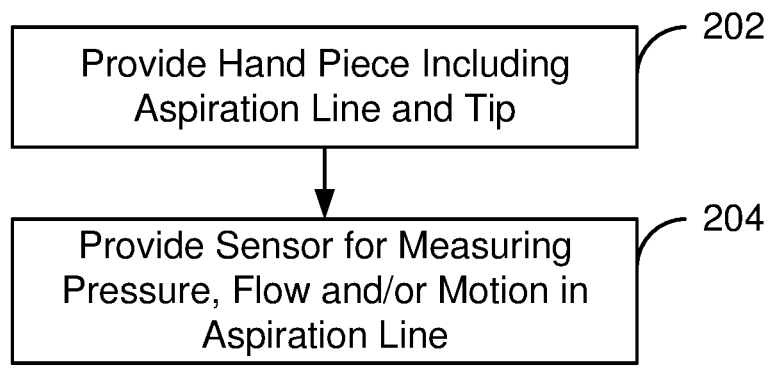
FIG. 4 is a flow chart depicting an exemplary embodiment of a method for providing a surgical hand piece.

FIG. 4 is an exemplary embodiment of a method 200 for providing a surgical hand piece such as the surgical hand piece(s) 100, 100' and/or 100″. For simplicity, some steps may be omitted, interleaved, and/or combined. The method 200 is also described in the context of the surgical hand piece 100. However, the method 200 may be used to form the surgical hand pieces 100', 100″ and/or an analogous surgical hand piece.

A hand piece 100' including an aspiration line 150 is provided, via step 202. Step 202 may include forming the body 120 and providing the irrigation line 140. In some embodiments, the irrigation line 140 may be integrated into the body 120. The cap 130 and tip configured to fit the body are provided.

The sensor(s) 160, 162 and/or 164 are also provided and placed in the appropriate portion of the hand piece 100, via step 204. Using the method 200, the surgical hand piece 100, 100' and/or 100' may be fabricated. Thus, the benefits of one or more of the surgical hand pieces 100, 100' and/or 100' may be achieved.

Figure 5:
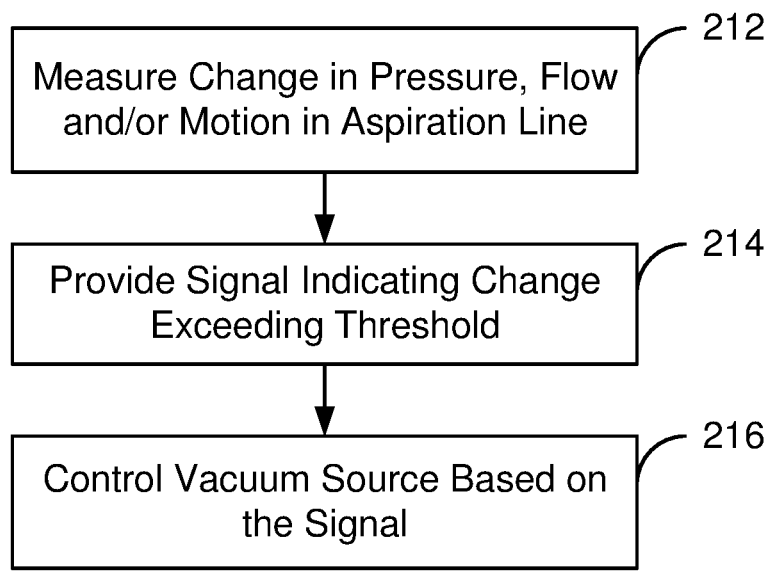
FIG. 5 is a flow chart depicting an exemplary embodiment of a method for assisting a physician using a surgical hand piece.

FIG. 5 is a flow chart depicting an exemplary embodiment of a method 210 for assisting a physician during ophthalmic surgery using a hand piece such as the hand piece 100, 100' and/or 100″. For simplicity, some steps may be omitted, interleaved, performed in another order and/or combined. The method 210 may include executing instructions on one or more processors. Further, the method 210 is described in the context of ophthalmic surgery. However, the method 210 may be extended to other types of surgery.

The method commences after surgery has started. Thus, the surgeon has made an incision in the eye of the patient, performed other required tasks, and inserted the appropriate portion of the tip 110 into the eye. In addition, the surgeon may have activated the vacuum source 106 and the fluid source 104. The surgeon may be in the process of breaking up and removing a cataract or extracting silicone oil from the eye of the patient.

A change in flow through the aspiration line, the pressure in the aspiration line and/or the motion of component 170 within the aspiration line is measured using sensor(s) 160, 162 and/or 164 in the aspiration line 150, via step 212.

A signal is provide from the sensor(s) 160, 162 and/or 164, via step 214. The signal indicates a change in pressure, flow and/or motion of a portion 170 of the hand piece 100. For example, the signal might indicated a reduction in pressure or an increase in piston speed. In some embodiments, the signal is provided in response to the change of at least a threshold being detected by the sensor(s) 160, 162 and/or 164. In other embodiments, the signal is provided by the sensor(s) 160, 162 and/or 164 without regard to the threshold and another component such as the control block 108 determines whether the threshold is exceeded.

The vacuum source 106 may be controlled based on the signal, via step 216. For example, the vacuum source 106 may be controlled to reduce the vacuum (i.e. increase the pressure) in the aspiration line in response to the threshold being met or exceeded. In particular, the control block 108 may automatically manage the vacuum source 106 to reduce the suction in the aspiration line 150.

Using the method 210 and the surgical hand piece 100, 100' and/or 100", changes in the speed of the piston 170 within the aspiration line 150 or changes in pressure in the aspiration line may rapidly and automatically result in a reduction in suction applied by the vacuum source 106. Thus, the patient's eye may be less likely to suffer collapse. Further, the surgeon is relieved of the burden of constantly and closely monitoring the pressure within the eye or aspiration line 150. Thus, ophthalmic surgery may be facilitated and patient safety may be improved. A method and system for providing a hand piece that can assist a surgeon, particularly for ophthalmic surgery, have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

I claim:

1. A surgical hand piece, comprising:
   an aspiration line;
   a sensor residing in the aspiration line, the sensor for measuring a change in velocity of a piston of the surgical hand piece within the aspiration line, wherein the sensor is selected from a Hall effect sensor, a Hall effect encoder, an accelerometer, and an optical motion sensor; and
   a tip coupled with the aspiration line.

2. The surgical hand piece of claim 1, wherein the change is at least one hundred percent of the velocity of the piston of the surgical hand piece within the aspiration line.

3. The surgical hand piece of claim 1, wherein the sensor is a first sensor and the surgical hand piece further comprises a second sensor that is configured to measure a change in pressure in the aspiration line.

4. The surgical hand piece of claim 3, further comprising an aspiration tube connector, wherein:
   a portion of the aspiration line resides in the aspiration tube connector; and
   the first or second sensor resides in the portion of the aspiration line residing in the aspiration tube connector.

5. The surgical hand piece of claim 1, wherein:
   the sensor provides a signal in response to the change; and
   a vacuum source is controlled in response to the signal.

6. The surgical hand piece of claim 1 further comprising an irrigation line coupled with the tip.

7. The surgical hand piece of claim 1, wherein the sensor is configured to initiate a signal in response to the change in velocity reaching or exceeding a pre-determined threshold.

8. The surgical hand piece of claim 1, wherein the sensor is configured to initiate a signal in response to a change in velocity of at least fifty percent.

9. The surgical hand piece of claim 1, wherein the sensor is configured to continuously provide a signal indicating the change in velocity of the piston of the surgical hand piece.

10. A surgical hand piece, comprising:
    an irrigation line;
    an aspiration line;
    a piston residing in the aspiration line;
    a motion sensor residing in the aspiration line, the motion sensor for measuring a change of at least one hundred percent in speed of the piston within the aspiration line, the motion sensor being selected from a Hall effect sensor, a Hall effect encoder, an accelerometer, and an optical motion sensor; and
    a tip coupled with the aspiration line and the irrigation line, a portion of the tip being configured to be inserted into a patient's eye, the motion sensor providing a signal in response to the change and wherein a vacuum source is controlled to reduce a vacuum in response to the signal.

11. The surgical system of claim 10, wherein the change in speed of the piston within the aspiration line is a change of at least one hundred percent.

12. The surgical system of claim 10, further comprising a console at least partially housing the controller.

13. The surgical system of claim 10, wherein the motion sensor is configured to initiate the signal in response to the change in speed of the piston reaching or exceeding a pre-determined threshold.

14. The surgical system of claim 10, wherein the motion sensor is configured to initiate the signal in response to the change in speed of the piston being an increase of at least fifty percent.

15. The surgical system of claim 10, wherein the motion sensor is configured to initiate the signal in response to the change in speed of the piston being an increase of at least one hundred percent.

* * * * *